(12) United States Patent
Hedlund et al.

(10) Patent No.: US 9,918,701 B2
(45) Date of Patent: Mar. 20, 2018

(54) METHODS AND SYSTEMS FOR AUTOMATIC CONTROL OF SUBJECTIVE IMAGE QUALITY IN IMAGING OF OBJECTS

(71) Applicant: ContextVision AB, Linköping (SE)

(72) Inventors: Martin Hedlund, Linköping (SE); Gunmar Farnebäck, Linköping (SE); Martin Kempe, Linköping (SE); Sharok Kimiaei, Hägersten (SE); Peter Kövamees, Adelsö (SE)

(73) Assignee: CONTEXTVISION AB, Linköping (SE)

(*) Notice: Subject to any disclaimer, the term of this patent is extended or adjusted under 35 U.S.C. 154(b) by 0 days.

(21) Appl. No.: 15/403,806

(22) Filed: Jan. 11, 2017

(65) Prior Publication Data
US 2017/0143312 A1    May 25, 2017

Related U.S. Application Data (63) Continuation-in-part of application No. 14/476,406, filed on Sep. 3, 2014, now Pat. No. 9,743,911.

(51) Int. Cl.
*A61B 8/00*    (2006.01)
*G06T 7/00*    (2017.01)
(Continued)

(52) U.S. Cl.
CPC .............. *A61B 8/54* (2013.01); *A61B 5/0035* (2013.01); *A61B 5/055* (2013.01); *A61B 5/4312* (2013.01);
(Continued)

(58) Field of Classification Search
CPC ......... A61B 8/54; A61B 6/037; A61B 5/4312; A61B 5/055; A61B 6/032; A61B 6/545;
(Continued)

(56) References Cited

U.S. PATENT DOCUMENTS

| | | |
|---|---|---|
| 5,579,768 A | 12/1996 | Klesenski |
| 5,993,392 A | 11/1999 | Roundhill et al. |

(Continued)

OTHER PUBLICATIONS

Zheng et al., A Regression Framework for Learning Ranking Functions Using Relative Relevance Judgments, ACM SIGIR Conference, Jul. 23-27, 2007, pp. 1-8, Amsterdam, The Netherlands.

*Primary Examiner* — Sanjay Cattungal
(74) *Attorney, Agent, or Firm* — Birch, Stewart, Kolasch & Birch, LLP (57) ABSTRACT

The present invention relates to method and system for automatic control of image quality in imaging of an object using, for example, an ultrasound system. The method comprises transmitting image generating signals into the object using selected system parameter sets of the imaging system. The imaging system has a number of different system parameter sets based on an image ranking measure reflecting a subjective expert opinion of a pre-defined set of images. The captured images are analyzed with respect to at least one image quality feature to determine an image quality metric for each image. The respective image quality metric for each image are analyzed to identify an image associated with a highest image quality metric and the system parameter set used for generating the image associated with the highest image quality metric can be selected as system parameter set for imaging of the object.

32 Claims, 8 Drawing Sheets

(51) Int. Cl.
  *A61B 5/055* (2006.01)
  *A61B 5/00* (2006.01)
  *A61B 6/03* (2006.01)
  *A61B 6/00* (2006.01)
  *A61B 8/14* (2006.01)
  *G06N 3/08* (2006.01)
  *G06N 3/04* (2006.01)

(52) U.S. Cl.
  CPC .............. *A61B 6/032* (2013.01); *A61B 6/037* (2013.01); *A61B 6/487* (2013.01); *A61B 6/545* (2013.01); *A61B 8/14* (2013.01); *G06N 3/0445* (2013.01); *G06N 3/08* (2013.01); *G06T 7/0012* (2013.01); *G06T 2207/10132* (2013.01); *G06T 2207/20081* (2013.01); *G06T 2207/20084* (2013.01)

(58) Field of Classification Search
  CPC ......... A61B 6/487; A61B 8/14; A61B 5/0035; G06T 7/0012; G06T 2207/20084; G06T 2207/10132; G06T 2207/20081; G06N 3/0445; G06N 3/08

USPC ........................... 600/437–469; 382/128–132
  See application file for complete search history.

(56) References Cited

U.S. PATENT DOCUMENTS

| | | |
|---|---|---|
| 6,200,267 B1 | 3/2001 | Burke |
| 6,743,174 B2 | 6/2004 | Ng et al. |
| 8,090,165 B2 | 1/2012 | Jiang et al. |
| 8,235,905 B2 | 8/2012 | Lin et al. |
| 8,357,094 B2 | 1/2013 | Mo et al. |
| 2003/0154062 A1 | 8/2003 | Daft et al. |
| 2008/0306385 A1 | 12/2008 | Jago et al. |
| 2010/0305441 A1 | 12/2010 | Lin et al. |
| 2012/0197122 A1* | 8/2012 | Kurt ...................... A61B 8/467 600/440 |

* cited by examiner

METHODS AND SYSTEMS FOR AUTOMATIC CONTROL OF SUBJECTIVE IMAGE QUALITY IN IMAGING OF OBJECTS

CROSS-REFERENCE RELATED APPLICATION

This application is a Continuation-In-Part of pending U.S. patent application Ser. No. 14/476,406, filed on Sep. 3, 2014. The entire contents of which are hereby incorporated by reference.

TECHNICAL FIELD

The present invention relates generally to imaging systems and method for such systems. More particularly, the present invention relates to methods and systems for automatic image optimization in imaging systems. Certain aspects of the present invention relates to methods and systems for automatic image optimization in ultrasound imaging systems.

BACKGROUND OF THE INVENTION

The use of ultrasound to produce images for medical monitoring and diagnosis has become wide spread to a large extent as a result from its nonionizing nature and its ability to produce images resulting from the inherent differences in properties of various soft tissues. Typical and common applications include examination and monitoring of the heart, abdomen and fetus. In most areas, diagnosis is now generally based on the size, position, contour and motion of the studied structures as well as on their relative transmission and reflection properties.

In general, for a typical ultrasound scanner, a user needs to perform multiple operations to obtain optimized images, which is time consuming and operator dependent. Furthermore, an inexperienced user may generate sub-optimal images due to sub-optimal settings that may increase the risk of an incorrect diagnosis.

In order to cope with these problems, a common procedure and practice is to use pre-set system parameters for the imaging procedure for each clinical application. In this case, the scanner may provide a good performance on an average patient without any user input. However, this approach does not take into account any patient specific variations, which in fact is very important in ultrasound imaging to obtain an optimal image quality.

In the prior art, there have been made a large number of attempts to provide automatic image optimization. For example, in U.S. Pat. No. 8,235,905 to Feng et al. discloses methods and systems for automatic image optimization for ultrasound imaging including evaluation of an image quality cost function in order to produce an image duality metric. The image quality metric is used to compare different images with each other to determine whether a maximized image quality metric has been reached. The signal, parameters that produced the maximized image quality metric are assigned as optimum parameters.

U.S. Pat. No. 5,579,768 to Klesensi discloses methods and systems for automatic gain compensation in an ultrasound imaging system. Imaging data is partitioned into small zones (e.g. such as regions selected in response to range and in response to azimuth, or both). At least one zone imaging value is determined for each zone corresponding to at least one measure of an imaging value for the signals reflected from objects or structures being imaged in that zone. The measures can be mean value or standard deviation. The imaging value can be an intensity value. Each zone is examined to determine whether its imaging values are within selected numeric range. An attenuation curve is formed in response to the selected zone intensity values. A gain compensation curve is determined from the attenuation curve.

U.S. Pat. No. 5,993,392 to Roundhill et al. discloses methods and systems for variation of dynamic range of ultrasonic image data as function of scanning depth and lateral dimension. The displayed dynamic range and noise rejection level are varied with both range (depth) and lateral (scanline to scanline) dimensions of an ultrasonic image.

U.S. Pat. No. 6,743,174 to Ng et al. is directed to automatic compensation for variations in brightness or contrast in ultrasonic diagnostic images. This is performed by computing offsets to a nominal TGC ("Time Gain Compensation") curve which will compensate for depth dependent attenuation. The offsets to the TGC curve are then applied to subsequent images. Image dynamic range may alternatively be used for the optimization. In particular, line fit is used and scanlines exhibiting poor coupling or low signal levels are discarded and the line fit is executed on the retained data. A linear slope is fitted to the depth-dependent attenuation characteristics of each scanline in the image and these slopes are combined in to a single slope value for the image.

U.S. Pat. No. 8,357,094 discloses methods and systems for adaptive system parameter optimization of ultrasound imaging systems. Fuzzy logic is used to adaptively adjust system parameters for imaging modes. A neural network may perform certain functions separately or in conjunction with the fuzzy logic. The neural network is configured to adapt functions of ultrasound image generating systems based on patient type, user preference and system operating conditions. The neural network is used in applications including detection of anatomical features, e.g. a main vessel, disease classification, and selection of features from different image modalities to obtain a composite image.

U.S. Pat. No. 8,090,165 to Jiang et al, is directed to gray-scale optimization of ultrasonic images. A searching device is arranged to search non-evenly divided sub-areas in an ultrasonic image. An analyzing device is arranged to analyze a change of gray level in each sub-area in the direction of depth. Based on the analysis, an optimized gray level value is calculated. In particular, the noise level is analyzed, a grey level changing curve (in a direction of depth) is analyzed, and, a PDM is obtained for the image, where PDM is an abbreviation for "Parameter for Digital Time Gain Compensation Module".

However, despite these numerous prior art methods and systems there is still a need for improved methods and systems for automatic control and optimization of system parameters of ultrasound imaging systems.

SUMMARY OF THE INVENTION

According to an object of the present invention, there is provided improved methods and systems for automatic control and optimization of scan or system parameters of ultrasound imaging systems.

According to other objects of the present invention there is provided improved method and systems for automatic control and optimization of system parameters of scanning or imaging systems or technologies including MRI (magnetic resonance imaging), CT (computed tomography), XR (X-ray radiation) fluoroscopy, PET (positron emission tomography), mammography and US (ultrasound).

These and other objects are achieved in accordance with the appended claims.

In the context of the present invention, the term "system parameter" refers to parameters that influences or controls the visual representation of the image. These parameters may affect the physical properties in the acquisition of the data (such as frequency and pulse frequency) but also the reconstruction of the signal (such as for example adjustment of dynamic range and Time Gain Correction) and post-processing (such as tuning of the image enhancement).

According to an aspect of the invention, there is provided a control system for automatic control of image quality in ultrasound imaging of at least one object using an ultrasound system including a transmitter/receiver for transmitting/receiving ultrasound image signals into the at least one object/from the at least one object using system parameter sets of the ultrasound system, and an ultrasound image processor configured to process the sets of signals into ultrasound images, wherein: the transmitter/receiver is configured to transmit/receive ultrasound image signals into the at least one object/from the at least one object using preferred sets of system parameters selected according to at least one subjective expert opinion; the ultrasound image processor is configured to process the received signals into a number of ultrasound images reflecting the subjective expert opinion; a training data generator is configured to generate sets of image variations for training based on different sets of system parameters; and a neural network is configured to: process data representing the images reflecting the subjective expert opinion and the image variations for training, for each set of image variations for training, auto-identify image features that correlate to image features of the ultrasound images reflecting the subjective expert opinion, and create a trained network comprising the auto-identified image features, wherein the trained network is configured to use the auto-identified image features to provide corrections for system parameters, said corrections predicting how to modify system parameters to obtain system parameters reflecting desired subjective expert image preferences.

According to embodiments of the present invention, an expert unit is configured to use the trained network to modify current system parameters of an ultrasound system based on the predicted corrections of the system parameters and to use the modified system parameters for creating new images.

According to embodiments of the present invention, the neural network is a convolutional neural network or recurrent neural network.

According to embodiments of the present invention, the training data generator is configured to generate the sets of system parameters according to a predetermined algorithm.

According to embodiments of the present invention, the training data generator is configured to use an algorithm that randomly samples system parameter values around the system parameters selected according to at least one subjective expert opinion to generate the sets of system parameters.

According to embodiments of the present invention, the data representing the images is one-dimensional, two-dimensional data, three-dimensional data, or four-dimensional data, wherein the data includes spatial and/or temporal data.

According to embodiments of the present invention, the data representing the images is intensity based data.

According to embodiments of the present invention, the system parameters include image enhance filtering, compounding, speed of sound, frequency, line density, harmonic imaging mode, and/or persistence.

According to embodiments of the present invention, the system parameters include gain, time gain compensation, dynamic range, and/or lateral gain control.

According to a further aspect of the present invention, there is provided a control system for automatic control of image quality in imaging of at least one object using an imaging system including signal generator for generating and transmitting image generating signals into the object using selected system parameter sets of the imaging system, a signal receiver for receiving sets of signals from the object and an image processor configured to process the sets of signals into images, wherein: the signal generator/signal receiver is configured to transmit/receive image signals into the at least one object/from the at least one object using preferred sets of system parameters selected according to at least one subjective expert opinion; the image processor is configured to process the received signals into a number of images reflecting the subjective expert opinion; a training data generator is configured to generate sets of image variations for training based on different sets of system parameters; and a neural network is configured to: process data representing the images reflecting the subjective expert opinion and the image variations for training, for each set of image variations for training, auto-identify image features that correlate to image features of the images reflecting the subjective expert opinion, and create a trained network comprising the auto-identified image features, wherein the trained network is configured to use the auto-identified image features to provide corrections for system parameters, said corrections predicting how to modify system parameters to obtain system parameters reflecting desired subjective expert image preferences.

According to embodiments of the present invention, an expert unit is configured to use the trained network to modify current system parameters of an imaging system based on the predicted corrections of the system parameters and to use the modified system parameters for creating new images.

According to embodiments of the present invention, the neural network is a convolutional neural network or recurrent neural network.

According to embodiments of the present invention, the training data generator is configured to generate the sets of system parameters according to a predetermined algorithm.

According to embodiments of the present invention, the training data generator is configured to use an algorithm that randomly samples system parameter values around the system parameters selected according to at least one subjective expert opinion to generate the sets of system parameters.

According to embodiments of the present invention, the data representing the images is one-dimensional, two-dimensional data, three-dimensional data, or four-dimensional data, wherein the data includes spatial and/or temporal data.

In embodiments of the control system according the present invention, the imaging system comprises at least one of a Ultrasound system, an MRI (magnetic resonance imaging) system, a CT (computed tomography) system, an XR (X-ray radiation) system, a fluoroscopy imaging system, a PET (positron emission tomography) system, or a mammography imaging system.

According to embodiments of the present invention, values for each image quality feature are calculated and an image quality metric is calculated for each, image based on the value for at least one image quality feature. The image quality features are correlated with the subjective expert opinion and may include contrast, sharpness, brightness, and/or presence of simple and complex structures that are likely to give a response in the human visual system (HVS). If presence of such simple and complex structures is used as image feature (or features), the image quality can be determined, at least partly, with use of so called GOP (General Operator Processor) technology. This technology is described, for example, in EP 86850180 "Apparatus for determining the degree of variation of a feature in a region of an image that is divided into discrete picture elements", to Knutsson et al., EP86850181, "Apparatus for determining the degree of consistency of a feature in a region of an image that is divided into discrete picture elements", to Knutsson et al., and EP86850182, "Apparatus for detecting sudden changes of a feature in a region of an image that is divided into discrete picture elements", to Knutsson et al., which hereby are incorporated in its entirety.

According to embodiments of the present invention, in order to find image features that are correlated with the expert opinion, selected images of the pre-defined set of ultrasound images, i.e. the images used to obtain the expert opinion are analyzed with respect to a set of predetermined image features. The image features are matched to the image ranking measures in a learning system and the level of correlation of image quality features is then determined based on the matching. For example, in a learning system, for example, using GBRank described by Z. Zheng, H. Zha, K. Chen, G. Sun "A regression framework for learning ranking functions using relative relevance judgements", ACM SIGIR Conference, Amsterdam, 2007.

The learning system may be implemented in the expert unit and there are a number of possible learning systems that can be used in the present invention such as methods including Ranking SVM (RankSVM), Rank post, FRank, RankRLS, SSRankBoost, SortNet, MPBoost, and GBlend. Methods such as IntervalRank and CRR are also conceivable. Furthermore, methods such as MCRank, Pranking, RankCosine, RankGP, PermuRank, SoftRank, Bolt Rank, BayesRank and NDCG Boost are also conceivable. It should however be noted that these examples are a non-exhaustive list of possible learning systems that can be used in the present invention and that there are, of course, other learning methods and system that are conceivable to use.

Further, in the matching of the image features to the image ranking measures in a learning system, the image features are given weights according to correlation to image ranking measure, wherein a higher image ranking measure results in a higher weight of an image feature.

The present invention is preferably used for two-dimensional imaging, three-dimensional imaging and four-dimensional, imaging (i.e. three dimensional images that varies over time) of objects or parts of objects.

Further advantageous embodiments of the device according to the present invention and further advantages with the present invention emerge from the dependent claims and the detailed description of embodiments.

BRIEF DESCRIPTION OF THE DRAWINGS

The present invention will now be described, for exemplary purposes, in more detail by way of embodiments and with reference to the enclosed drawings, in which.

DETAILED DESCRIPTION OF EMBODIMENTS

In the drawings, similar or corresponding elements are denoted by the same reference numbers.

Figure 1:
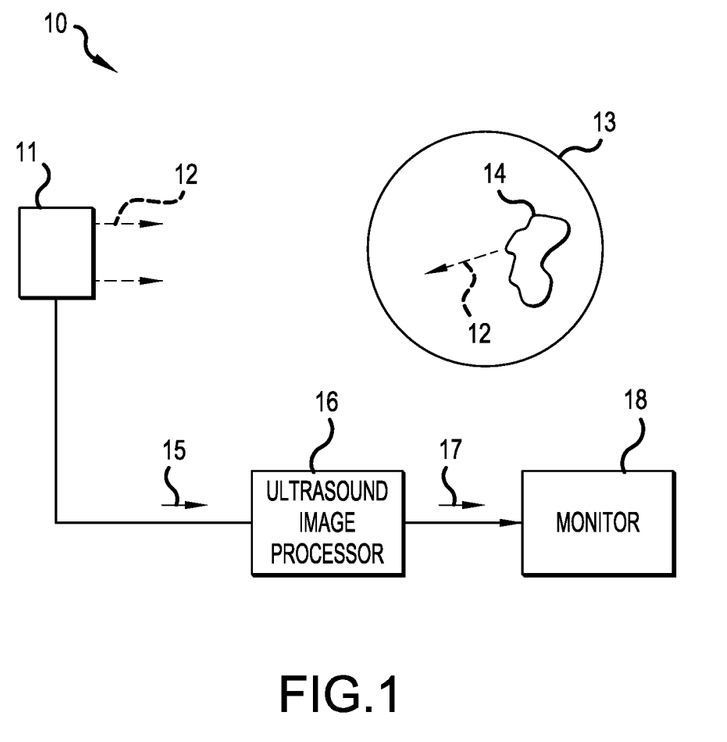
FIG. 1 is a schematic view of a general ultrasound imaging system in which the present invention may be implemented.

With reference first to FIG. 1, a general ultrasound imaging system in which the present invention can be implemented will be discussed. An ultrasound system 10 comprises a probe 11, including for example, an ultrasound transducer array having a set of transducer elements, for generating ultrasound acoustic signals 12 that are typically directed in a scan plane 13, e.g. behind a skin surface or in a body cavity such as in the human body. Although a 20 scan plane 13 is described, the scan plane 13 may also comprise a 30 scan region.

The acoustic signals 12 are reflected by objects or structures 14 in the scan plane 13 and return to the probe 11 or the transducer elements). The transducer elements in the probe 11 convert the reflected ultrasound acoustic signals 12 into a set of corresponding electrical signals 15, and transmit those signals 15 to an ultrasound image processor 16. The ultrasound image processor 16 produces, in response to the electrical signals 15, a display signal 17, which is transmitted to a display device 18 (such as a monitor) for display to an operator.

Figure 2:
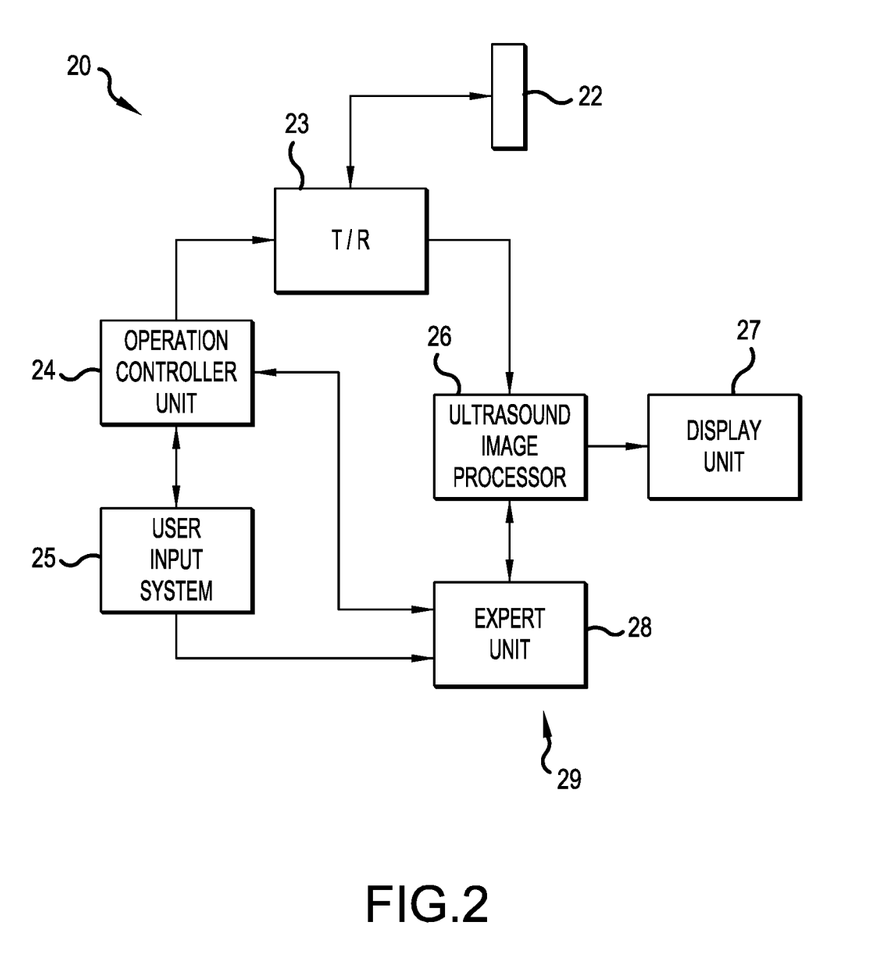
FIG. 2 is a schematic view of an embodiment of an ultrasound imaging system incorporating the present invention.

With reference to FIG. 2, an embodiment of an ultrasound imaging system 20 incorporating various features of the present invention will be discussed. The ultrasound imaging system 20 according to the present invention includes a transducer array 22 including a plurality of separately driven transducer elements, each of which produces a burst of ultrasonic energy when energized by a pulsed waveform produced by a transmitter. Traditionally, ultrasound transducers have been made of piezoelectric ceramic. However, silicon transducers or capacitive micromachined ultrasonic transducers (CMUT) is also conceivable as an alternative to the piezoelectric transducers.

The transducer array 22 may be arranged in a handheld probe. The ultrasonic energy reflected back to the transducer array 22 from the object under study is converted to an electrical signal by each receiving transducer element and applied separately to a transmitter/receiver (T/R) 23. The transmitter/receiver 23 comprises a transmitter part including for example pulsars, aperture and voltage controller and the like. Further, the transmitter/receiver 23 comprises a receiver part including amplifiers, filters, demodulators, analog-to-digital conversion unit, image reconstruction (array focusing) module, and the like.

The transmitter/receiver 23 is operated under control of an operation controller unit 24 responsive to, commands from user input entered through a user input system 25. The operation control unit 24 usually communicate either directly or indirectly with all units of the system to synchronize their activities. The user input system provides user control mechanisms and units including, for example, console, keyboard, hard and soft keys, touch screen, foot pedals and voice control. An ultrasound image processor 26 processes signals from the transmitter/receiver 23 and sends the output to a display unit 27 such as a LCD or CRT monitor. The ultrasound image processor 26 includes detectors for different modes, filters, scan converter and the like. The system may further comprise a data and storage unit (not shown) including memory devices/buffers hard discs, micro discs and the like. The system may further include an external communication unit (not shown) providing interfaces to, for example, external storage or display devices including, for example, printer, VCR, DVD, MOD, workstation, the Internet and/or equipment for obtaining physiological signals such as ECG. A control system 29 according to the present invention may comprise an expert unit 28 communicates with the various components of the system 20 via bus(es), signal/data line(s), and the like.

The expert unit 28 is inter alfa configured to perform system parameter optimization functions based on a subjective expert opinion of ultrasound images, which will be described in more detail below. Specifically, based on image data from the ultrasound image processor 26, the expert unit 28 is configured to automatically adjust parameters in the transmitter/receiver 23 and/or ultrasound image processor 26. By automating the control of system parameters of the ultrasound imaging system 20, the efficiency, reproducibility and user-friendliness of the ultrasound imaging system 20 can be significantly improved and enhanced in comparison with a manual system. In a prior art manual system, the clinician will set the system or system parameters manually for the type of anatomy being diagnosed and the attenuation encountered (based on default values or will use the default values of the parameters). Each time a new object, or anatomy is viewed or a different depth of image is selected, it may be desirable to change the system parameters, such as for example time gain compensation, to produce a more, or improved diagnostic image.

Figure 3:
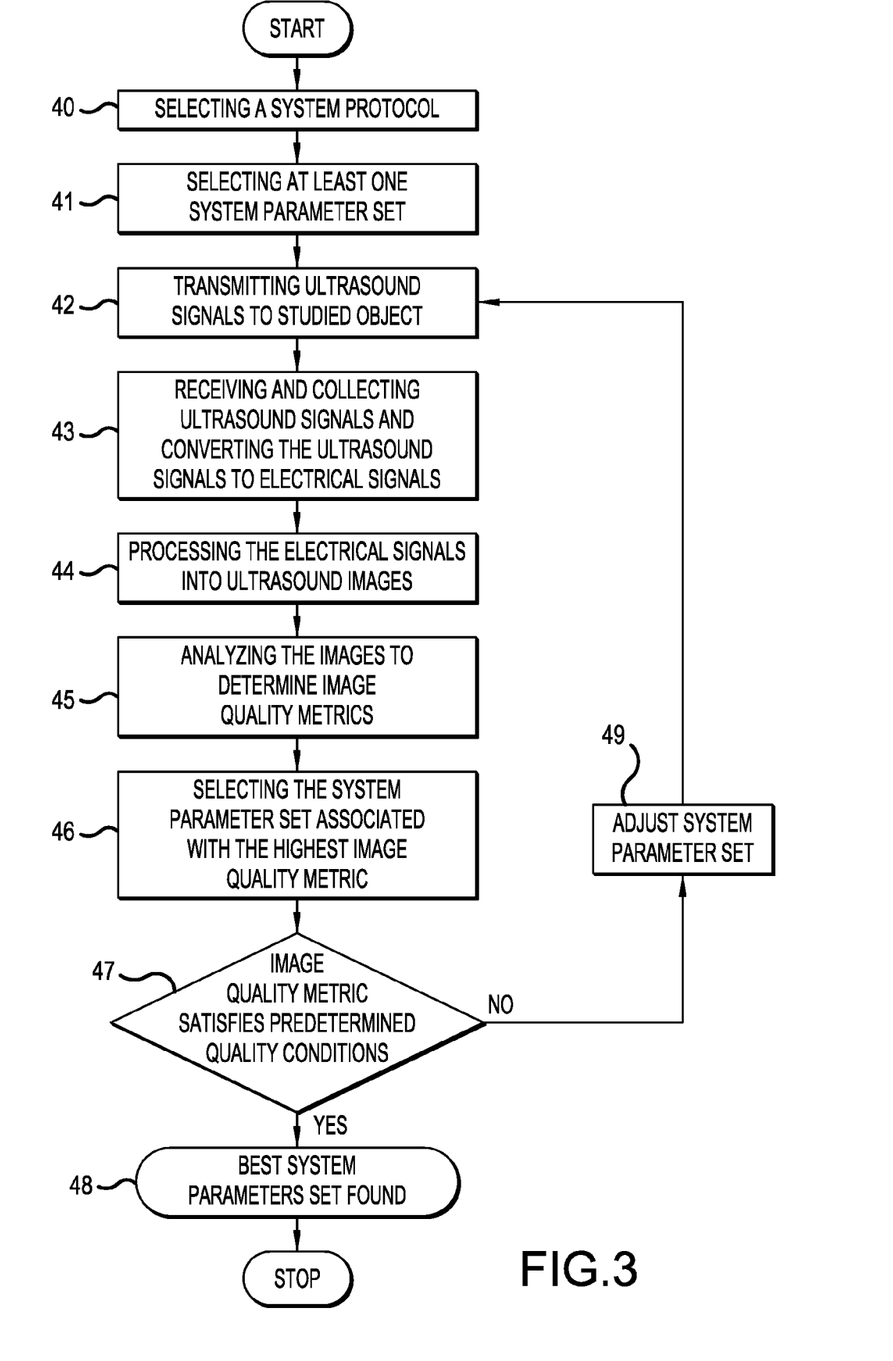
FIG. 3 is a flow chart illustrating the steps of a method for control and/or optimization of system parameters for ultrasound imaging according to embodiments of the present invention.
Figure 6:
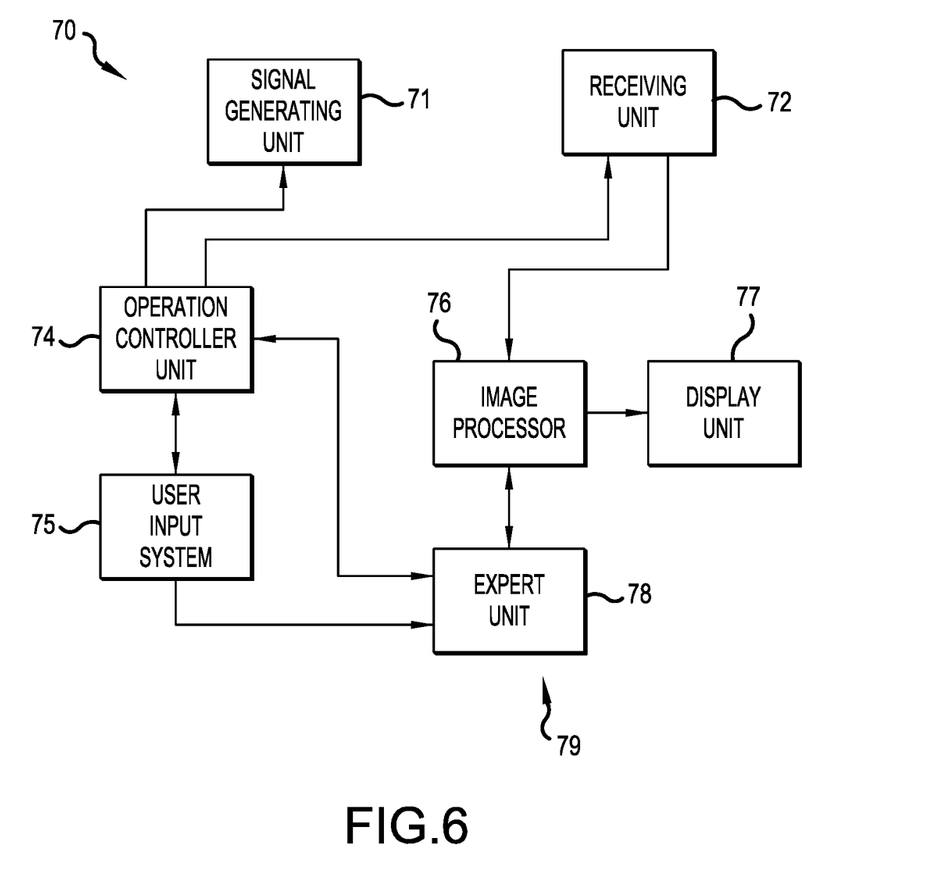
FIG. 6 is a schematic view of an embodiment of an imaging system incorporating the present invention.
Figure 7:
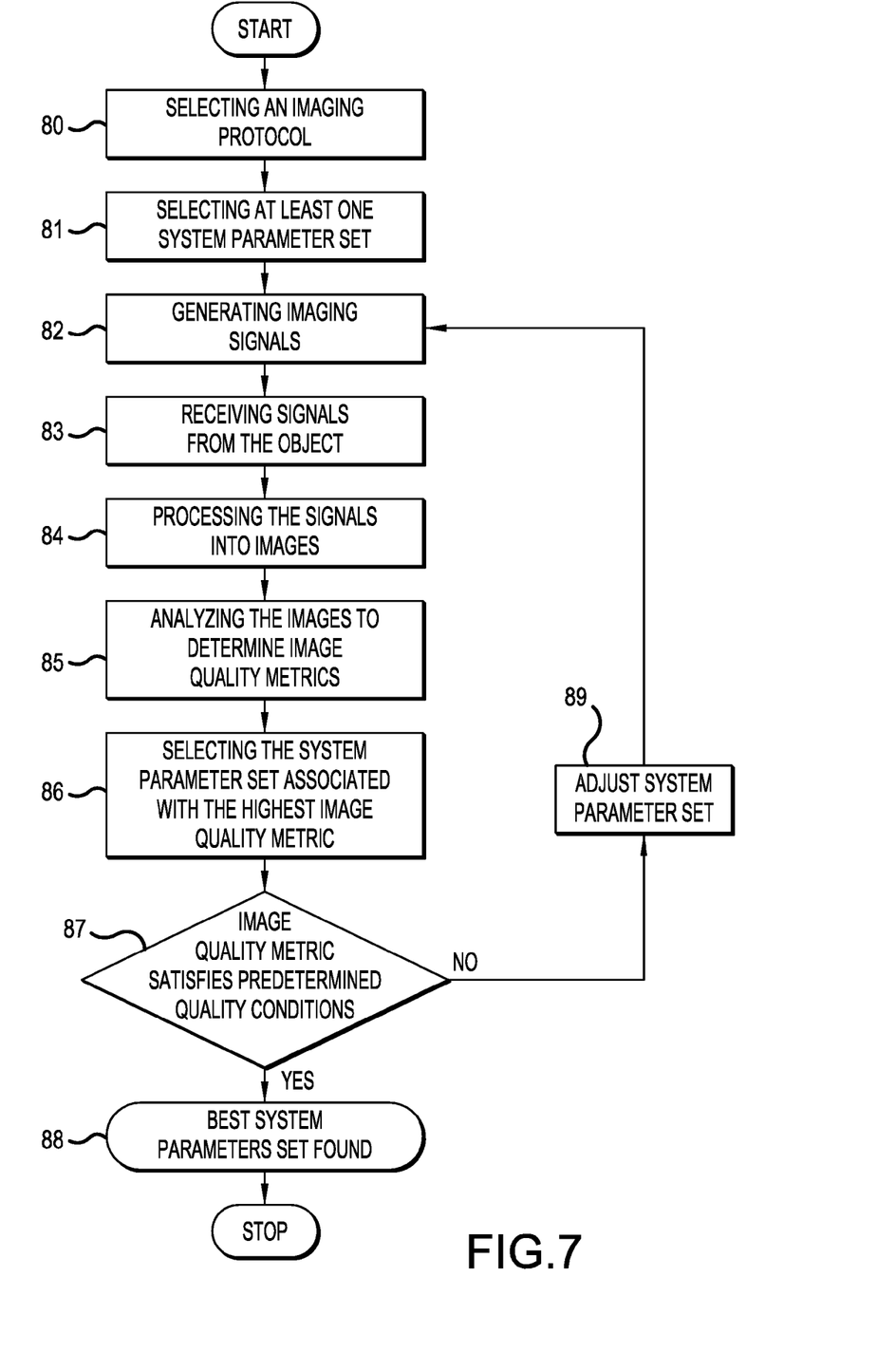
FIG. 7 is a flow chart illustrating the steps of a method for control and/or optimization of system parameters for an imaging system according to embodiments of the present invention.

With reference now to FIG. 3, a method for optimization and/or control of system parameters of an ultrasound imaging system in accordance with the present invention will be described. System parameter refers to parameters that influences or controls the visual representation of the image. These parameters may affect the physical properties in the acquisition of data (such as frequency and pulse frequency in an ultrasound system) but also the reconstruction of the signal (such as for example adjustment of dynamic range and Time Gain Correction in an ultrasound system) and post-processing (such as tuning of the image enhancement). One or several of these parameters can be used for optimizing the image quality. Thereby, the method and system according to the present invention can be used for one or several imaging modes such as imaging systems or technologies including MRI (magnetic resonance imaging), CT (computed tomography), XR (X-ray radiation), fluoroscopy, PET (positron emission tomography), mammography and US (ultrasound). Hence, even though the following examples of the present invention are implemented in an ultrasound imaging system, the present invention should not be regarded as limited to ultrasound systems. The present invention can be implemented in imaging systems where different resulting images can be generated based on one or several steps in an image generating chain using different system parameter values that affect the physical properties in the acquisition of data, the image reconstruction process and/or the post-processing process. With reference to FIGS. 6 and 7, the present invention is described in the context of a general imaging system.

FIG. 3 schematically illustrates a flow chart of an embodiment of a method according to the present invention. At step 40, a system protocol for the anatomy being studied is selected. The system protocol may for example be a protocol for imaging of a heart including a number of different system parameter sets. This selection may be automatic or may be a manual selection made by the clinician or operator. At step 41, at least one system parameter set is selected for the specific anatomy being studied based on an image ranking measure reflecting a subjective expert opinion of ultrasound images or manually set by the user, which will be described in more detail below. This selection of start or initial system parameters sets may be performed by the expert unit 28. Thereafter, at step 42, ultrasound image generating signals are transmitted from the transducer array 22 into the studied object using the selected system parameter sets. At step 43, reflected, ultrasound signals are received and collected and the ultrasound signals are converted to electrical signals representing the echoes of the ultrasound signals from the organs or structures within the object. At step 44, the sets of electrical signals are processed into ultrasound images in the ultrasound image processor 26, each image being associated with a specific system parameter set. Then, at step 45, the images are analyzed in the expert unit 28 with respect to at least one image quality feature to determine an image quality metric for each image. At step 46, the respective image quality metric for each image is analyzed with each other to identify an image associated, with the best image quality metric, for example, the highest image quality metric and the system parameter set used for generating the image associated with the best image quality metric is then selected as system parameter set for further ultrasound imaging of the object and the image may also be displayed on the display unit 27. At step 47, a decision is made by the expert unit 28 if the image quality metric satisfies at least one predetermined quality condition. For example, a predetermined quality condition may be that an improvement of the image quality metric is below a predetermined threshold.

If yes, the procedure is terminated and the identified system parameter set is determined to be the best or the desired and may be used for ultrasound imaging of the object at step 48. If no, the procedure proceeds to step 49, where new system parameter sets are created or the previous system parameters are adjusted. Alternatively, the created system parameter set can be compared with a new system parameter set or an adjusted system parameter set. Thus, the procedure returns to step 42. The operator or clinician may also terminate the procedure manually if desired, for example, if an image is determined to have a satisfying quality.

Figure 4:
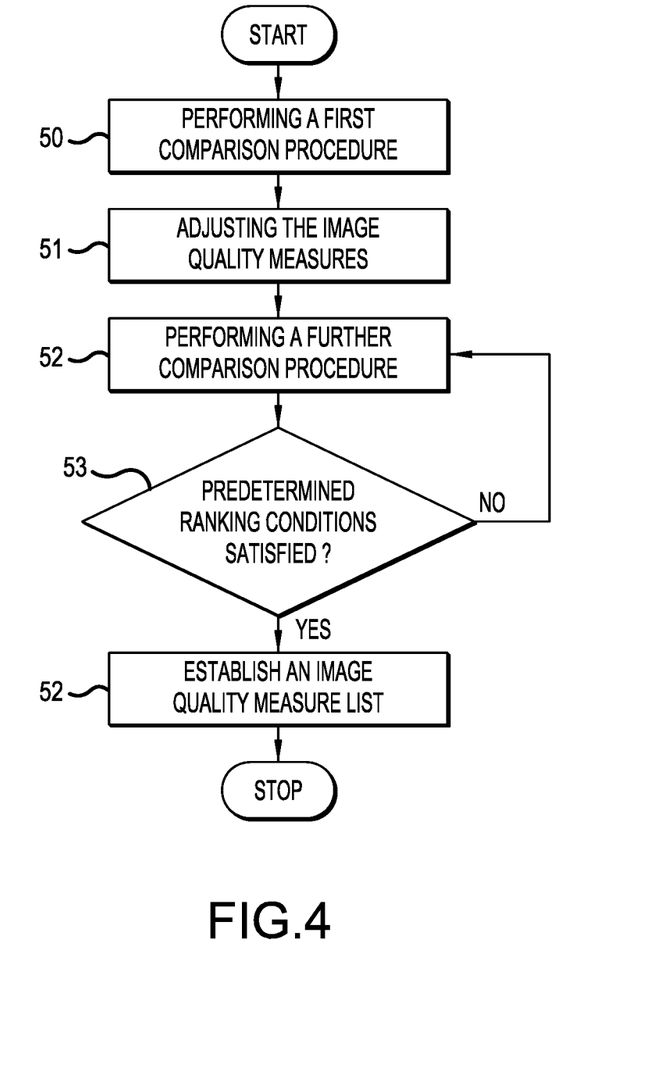
FIG. 4 is a flow chart illustrating steps of a method for quantifying subjective expert opinions of ultrasound image experts or clinicians according to embodiments of the present invention.

With reference to FIG. 4, a method for quantifying subjective expert opinions of ultrasound image experts or clinicians. The procedure for quantifying subjective expert opinions of ultrasound image experts or clinicians is based on a predetermined set of ultrasound images for at least one anatomy from different types of objects obtained with known system parameter sets, for example, known values for Overall Gain Control (G), Time Gain Control (TGC), Frequency (F) and Dynamic Range (DR). First, at step 50, matching or comparison between pairs of images is performed. Preferably, all images are compared, for example, sequentially, so as to allow the expert or the experts to, select the best image in each pair. Each image is associated with an image ranking measure indicating the quality of an image relative other images. Further, each image may also be associated with an uncertainty value that indicates the accuracy of the ranking position of an image. The uncertainty value may for example depend on the number of comparisons that have been made. In each comparison, the best image in terms of subjective quality (i.e. a winning image) is determined and the winning image is associated with a higher image ranking measure than the loosing image, i.e. the image determined to have a lower subjective quality. Each image may also be associated with a relative quality measure in order to speed up the ranking process. For example, each image may be associated with a relative quality measure based on visual quality in accordance with:

Visual grading: level 1=high;
Visual grading: level 2=medium
Visual grading: level 3=low In order to speed up the procedure, the number of images can be reduced by excluding, for example, the images having a visual grading of level 3. Thereafter, at step 51, the image quality measures are adjusted. For example, the images having a visual grading of level 1 is given a higher image quality measure than the images having a visual grading of level 2. At step 52, a second comparison procedure between selected pairs of images is performed. For example, the images are selected based on their respective uncertainty value. In each comparison, the best image in terms of subjective quality (i.e. a winning image) is determined and the winning image is associated with an increased image ranking measure and the loosing image, i.e. the image determined to have a lower subjective quality, is given a decreased image quality measure. At step 53, it is checked whether predetermined ranking conditions have been satisfied. For example, these may include if a predetermined lowest uncertainty value has been reached and/or a maximum number of comparisons have been performed and/or if all images have been compared with each other. If no, the procedure returns to step 52. On the other hand, if yes, the procedure proceeds to step 54 where an image quality measure list is established. In the image quality measure list, the images are ranked according to image quality measure, where the highest measure indicates the best image and lower measures indicate images having a lower degree of quality. This image quality measure list is used to train the expert unit 28 to reflect the opinion of at least one expert. For each type of object, the system parameter set that is judged to be best (i.e., generates an image having the highest image quality measure) is used as a start or initial set-up in ultrasound imaging. That is, this best or optimal system parameter set is used as starting or initial set-up for the control and/or optimization procedure described above with reference to FIG. 3.

Figure 5:
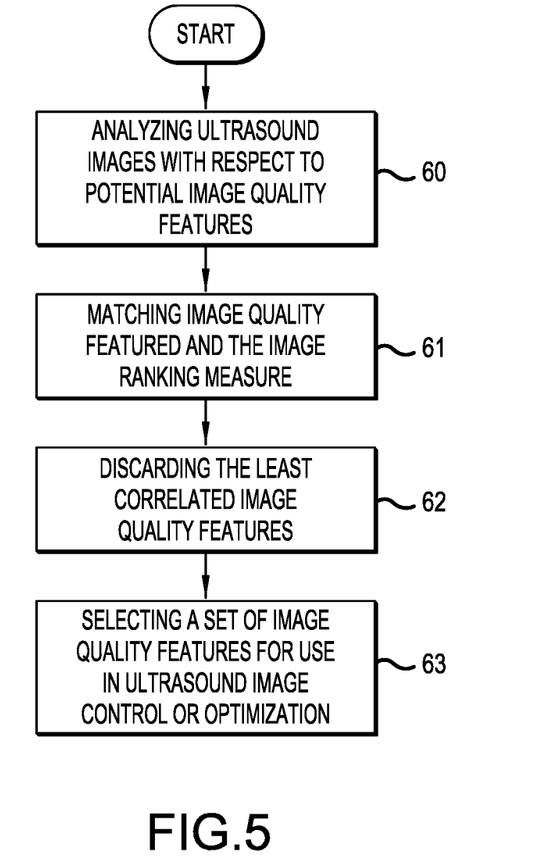
FIG. 5 is a flow chart illustrating steps of a method for identifying image quality features that are correlated, to the subjective expert opinions of ultrasound image experts or clinicians according to embodiments of the present invention.

With reference to FIG. 5, a method for identifying image quality features that are correlated to the subjective expert opinion of at least one ultrasound image expert or clinician. The corresponding set of images used in procedure for quantifying subjective expert opinions of ultrasound image experts or clinicians is used for identifying image quality features in a library of possible image quality features. In step 60, the images are analyzed with respect to the possible image quality features. At step 61, a matching between image quality feature values and the image ranking measure is performed in a learning system, for example, using GBRank described by Z. Zheng, Zha, K. Chen, G. Sun "A regression framework for learning ranking functions using relative relevance judgements", ACM SIGIR Conference, Amsterdam, 2007.

The learning system may be implemented in the expert unit 28. As discussed above, there are a number of possible learning systems that can be used in the present invention such as Ranking SVM (RankSVM), GBlend, IntervalRank, CRR, MCRank, Pranking, RankGP or NDCG Boost. It should however be noted that these examples are a non-exhaustive list of possible learning systems that can be used in the present invention and that there are, of course, other learning methods and system that are conceivable to use.

At step 62, the least correlated image quality features are discarded and, at step 63, a set of image quality features that are determined to correlate to the subjective expert opinions of the ultrasound experts are selected for use in ultrasound image control or optimization.

With reference to FIG. 6, an embodiment of an imaging system 70 incorporating various features of the present invention will be discussed. The imaging system 70 according to the present invention includes signal generating unit 71, for example, a unit generating magnetic fields or radiation in an MRI, CT, or XR system. Further, a receiving unit 72, e.g. a radiation detecting unit, is adapted to receive the signal, for example, attenuated X-rays from the object.

The signal generating unit 71 and the receiving unit 72 are operated under control of an operation controller unit 74 responsive to commands from user input entered through a user input system 75. The operation control unit 74 usually communicate either directly or indirectly with all units of the system to synchronize their activities. The user input system provides user control mechanisms and units including, for example, console, keyboard, hard and soft keys, touch screen, foot pedals and voice control. An image processor 76 processes signals from the receiving unit 72 and sends the output to a display unit 77 such as a LCD or CRT monitor.

The image processor 76 includes input for different modes, filters, scan converter and the like. The system may further comprise a data and storage unit (not shown) including memory devices/buffers hard discs, micro discs and the like. The system may further include an external communication unit (not shown) providing interfaces to, for example, external storage or display devices including, for example, printer, VCR, DVD, MOD, workstation, the Internet and/or equipment for obtaining physiological signals such as ECG. A control system 79 according to the present invention may comprise an expert unit 78 that communicates with the various components of the system 70 via bus(-es), signal/data line(s), and the like.

The expert unit 78 is inter alia configured to perform system parameter optimization functions based on a subjective expert opinion of the images (e.g. XR images), which will be described in more detail below. Specifically, based on image data from the image processor 76, the expert unit 78 is configured to automatically adjust parameters for the signal generating unit 71 and/or receiving unit 72 and/or image processor 76. By automating the control of system parameters of the imaging system 70 in accordance with the present invention, the efficiency, reproducibility and user-friendliness of the ultrasound imaging system 70 can be significantly improved and enhanced in comparison with a manual system where the clinician will set the scan or system parameters manually for the type of anatomy being diagnosed and the attenuation encountered (based on default values or will use the default values of the parameters).

With reference now to FIG. 7, a method for optimization and/or control of system parameters of an imaging system in accordance with the present invention will be described. As discussed above, system parameter refers to parameters that influences or controls the visual representation of the image and that may affect the physical properties in the acquisition of the data (such as dose, kVp and beam quality) but also the reconstruction of the signal and post-processing (such as image enhancement). One or several of these parameters can be used for optimizing the image quality. Thereby, the method and system according to the present invention can be used for one or several imaging modalities such as imaging systems or technologies including MRI (magnetic resonance imaging), CT (computed tomography), XR (X-ray radiation), fluoroscopy, PET (positron emission tomography), mammography and US (ultrasound).

FIG. 7 schematically illustrates a flow chart of a further embodiment of a method according to the present invention. At step 80, an imaging protocol for the anatomy being studied is selected. The imaging protocol may for example be a protocol for imaging of a heart including a number of different pre-set system parameter sets. This selection may be automatic or may be a manual selection made by the clinician or operator. At step 81, at least one system parameter set is selected for the specific anatomy being studied based on an image ranking measure reflecting a subjective selection of images, which will be described in more detail below. This selection of start or initial system parameters sets may be performed by the expert unit 78. Thereafter, at step 82, image generating signals are generated and provided to the studied object using the selected system parameter sets. At step 83, signals are received from the object and gathered and the received signals are converted to electrical signals representing the organs or structures within the object. At step 84, the sets of electrical signals are processed into images in the image processor 76, each image being associated with a system parameter set. Then, at step 85, the images are analyzed in the expert unit 78 with respect to at least one image quality feature to determine an image quality metric for each image. At step 86, the respective image quality metric for each image is analyzed with respect to each other to identify an image associated with the best image quality metric, for example, the highest image quality metric and the system parameter set used for generating the image associated with the best image quality metric is then selected as system parameter set for further imaging of the object and the image may also be displayed on the display unit 77. At step 87, a decision is made by the expert unit 78 if the image quality metric satisfies predetermined quality conditions. If yes, the procedure is terminated and the identified system parameter set is determined to be optimal and may be used for imaging of the object at step 88. If no, the procedure proceeds to step 89, where new system parameter sets are created, the previous system parameters are adjusted. Alternatively, the created system parameter set can be compared with a new system parameter set or an adjusted system parameter set in that the non-linear quality metrics for the respective resulting images are compared. Thus, the procedure returns to step 82. The operator or clinician may also manually further adjust, after or terminate the procedure manually if desired, for example, if an image is determined to have a satisfying quality.

Figure 8:
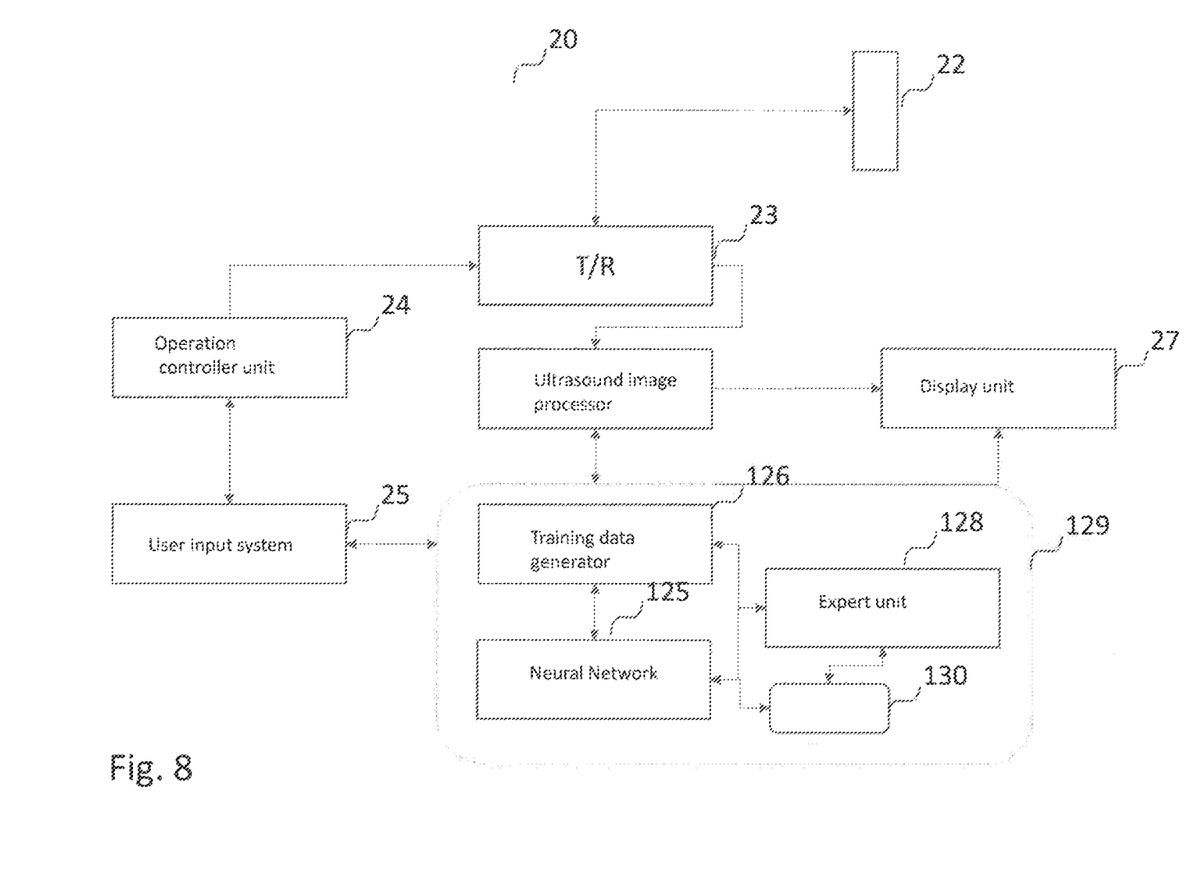
FIG. 8 is a schematic view of an embodiment of an imaging system incorporating the present invention.

With reference to FIG. 8, a control system 129 for automatic control of image quality in ultrasound imaging of at least one object using an ultrasound system 20 including a transmitter/receiver 23 for transmitting/receiving ultrasound image signals into the at least one object/from the at least one object using system parameter sets of the ultrasound system is shown. In other embodiments of the present invention, the imaging system comprises at least one of an MRI (magnetic resonance imaging) system, a CT (computed tomography) system, an XR (X-ray radiation) system, a fluoroscopy imaging system, a PET (positron emission tomography) system, or a mammography imaging system.

An ultrasound image processor 26 is configured to process the sets of signals into ultrasound images. The transmitter/receiver 23 is configured to transmit/receive ultrasound image signals into the at least one object/from the at least one object using preferred sets of system parameters selected according to at least one subjective expert opinion. The ultrasound image processor 26 is configured to process the received signals into a number of ultrasound images reflecting the subjective expert opinion. A training data generator 126 is configured to generate sets of image variations for training based on different sets of system parameters and a neural network 125 is configured to: process data representing the images reflecting the subjective expert opinion and the image variations for training, for each set of image variations for training, auto-identify image features that correlate to image features of the ultrasound images reflecting the subjective expert opinion, and create a trained network 130 comprising the auto-identified image features, wherein the trained network is configured to use the auto-identified image features to provide corrections for system parameters, said corrections predicting how to modify system parameters to obtain system parameters reflecting desired subjective expert image preferences.

Further, an expert unit 128 is configured to use the trained network 130 to modify current system parameters of an ultrasound system based on the predicted corrections of the system parameters and to use the modified system parameters for creating new images.

In embodiments using other imaging modalities, the transmitter/receiver is a signal generating and receiving device and the ultrasound image processor is an image processor. The image processor includes input for different modes, filters, scan converter and the like. The system may further comprise a data and storage unit (not shown) including memory devices/buffers hard discs, micro discs and the like. The system may further include an external communication unit (not shown) providing interfaces to, for example, external storage, or display devices including, for example, printer, VCR, DVD, MOD, workstation, the Internet and/or equipment for obtaining physiological signals such as ECG.

The invention shall not be considered limited to the embodiments illustrated, but can be modified and altered in many ways by one skilled in the art, without departing, from the scope of the appended claims.

The invention claimed is:

1. A control system for automatic control of image quality in ultrasound imaging of at least one object using an ultrasound system including a transmitter/receiver for transmitting/receiving ultrasound image signals into the at least one object/from the at least one object using system parameter sets of the ultrasound system, and an ultrasound image processor configured to process the sets of signals into ultrasound images, wherein:
   the transmitter/receiver is configured to transmit/receive ultrasound image signals into the at least one object/from the at least one object using preferred sets of system parameters selected according to at least one subjective expert opinion;

the ultrasound image processor is configured to process the received signals into a number of ultrasound images reflecting the subjective expert opinion;

a training data generator is configured to generate sets of image variations for training based on different sets of system parameters; and a neural network is configured to:

process data representing the images reflecting the subjective expert opinion and the image variations for training, for each set of image variations for training, auto-identify image features that correlate to image features of the ultrasound images reflecting the subjective expert opinion, and create a trained network comprising the auto-identified image features, wherein the trained network is configured to use the auto-identified image features to provide corrections for system parameters, said corrections predicting how to modify system parameters to obtain system parameters reflecting desired subjective expert image preferences.

2. The system according to claim 1, further comprising an expert unit using the trained network to modify current system parameters of an ultrasound system based on the predicted corrections of the system parameters and to use the modified system parameters for creating new images.

3. The system according to claim 1, wherein the neural network is a convolutional neural network or recurrent neural network.

4. The system according to claim 1, wherein the training data generator is configured to generate the sets of system parameters according to a predetermined algorithm.

5. The system according to claim 1, wherein the training data generator is configured to use an algorithm that randomly samples system parameter values around the system parameters selected according to at least one subjective expert opinion to generate the sets of system parameters.

6. The system according to claim 1, wherein the data representing the images is one-dimensional, two-dimensional data, three-dimensional data, or four-dimensional data, wherein the data includes spatial and/or temporal data.

7. The system according to claim 1, wherein the data representing the images is intensity based data.

8. The system according to claim 1, wherein the system parameters include image enhance filtering, compounding, speed of sound, frequency, line density, harmonic imaging mode, and/or persistence.

9. The system according to claim 7, wherein the system parameters include gain, time gain compensation, dynamic range, and/or lateral gain control.

10. A control system for automatic control of image quality in imaging of at least one object using an imaging system including signal generator for generating and transmitting image generating signals into the object using selected system parameter sets of the imaging system, a signal receiver for receiving sets of signals from the object and an image processor configured to process the sets of signals into images, wherein:

the signal generator/signal receiver is configured to transmit/receive image signals into the at least one object/from the at least one object using preferred sets of system parameters selected according to at least one subjective expert opinion;

the image processor is configured to process the received signals into a number of images reflecting the subjective expert opinion;

a training data generator is configured to generate sets of image variations for training based on different sets of system parameters; and a neural network is configured to:

process data representing the images reflecting the subjective expert opinion and the image variations for training, for each set of image variations for training, auto-identify image features that correlate to image features of the images reflecting the subjective expert opinion, and create a trained network comprising the auto-identified image features, wherein the trained network is configured to use the auto-identified image features to provide corrections for system parameters, said corrections predicting how to modify system parameters to obtain system parameters reflecting desired subjective expert image preferences.

11. The system according to claim 10, further comprising an expert unit using the trained network to modify current system parameters of an imaging system based on the predicted corrections of the system parameters and to use the modified system parameters for creating new images.

12. The system according to claim 10, wherein the neural network is a convolutional neural network or recurrent neural network.

13. The system according to claim 10, wherein the training data generator is configured to generate the sets of system parameters according to a predetermined algorithm.

14. The system according to claim 10, wherein the training data generator is configured to use an algorithm that randomly samples system parameter values around the system parameters selected according to at least one subjective expert opinion to generate the sets of system parameters.

15. The system according to claim 10, wherein the data representing the images is one-dimensional, two-dimensional data, three-dimensional data, or four-dimensional data, wherein the data includes spatial and/or temporal data.

16. The control system according to claim 10, wherein the imaging system comprises at least one of a Ultrasound system, an MRI (magnetic resonance imaging) system, a CT (computed tomography) system, an XR (X-ray radiation) system, a fluoroscopy imaging system, a PET (positron emission tomography) system, or a mammography imaging system.

17. A control method for automatic control of image quality in ultrasound imaging of at least one object using an ultrasound system including a transmitter/receiver for transmitting/receiving ultrasound image signals into the at least one object/from the at least one object using system parameter sets of the ultrasound system, and an ultrasound image processor configured to process the sets of signals into ultrasound images, wherein:

the transmitter/receiver is configured to transmit/receive ultrasound image signals into the at least one object/from the at least one object using preferred sets of system parameters selected according to at least one subjective expert opinion;

the ultrasound image processor is configured to process the received signals into a number of ultrasound images reflecting the subjective expert opinion;

generating, in a training data generator, sets of image variations for training based on different sets of system parameters; and, in a neural network:

processing data representing the images reflecting the subjective expert opinion and the image variations for training, for each set of image variations for training, auto-identifying image features that correlate to image features of the ultrasound images reflecting the subjective expert opinion, and creating a trained network comprising the auto-identified image features, wherein the trained network is configured to use the auto-identified image features to provide corrections for system parameters, said corrections predicting how to modify system parameters to obtain system parameters reflecting desired subjective expert image preferences.

18. The method according to claim 17, further comprising, in an expert unit, using the trained network to modify current system parameters of an ultrasound system based on the predicted corrections of the system parameters and to use the modified system parameters for creating new images.

19. The method according to claim 17, wherein the neural network is a convolutional neural network or recurrent neural network.

20. The method according to claim 17, further comprising generating, in the training data generator, the sets of system parameters according to a predetermined algorithm.

21. The method according to claim 17, further comprising using, in the training data generator, an algorithm that randomly samples system parameter values around the system parameters selected according to at least one subjective expert opinion to generate the sets of system parameters.

22. The method according to claim 17, wherein the data representing the images is one-dimensional, two-dimensional data, three-dimensional data, or four-dimensional data, wherein the data includes spatial and/or temporal data.

23. The method according to claim 17, wherein the data representing the images is intensity based data.

24. The method according to claim 17, wherein the system parameters include image enhance filtering, compounding, speed of sound, frequency, line density, harmonic imaging mode, and/or persistence.

25. The method according to claim 23, wherein the system parameters include gain, time gain compensation, dynamic range, and/or lateral gain control.

26. A control method for automatic control of image quality in imaging of at least one object using an imaging system including signal generator for generating and transmitting image generating signals into the object using selected system parameter sets of the imaging system, a signal receiver for receiving sets of signals from the object and an image processor configured to process the sets of signals into images, wherein:

the signal generator/signal receiver is configured to transmit/receive image signals into the at least one object/from the at least one object using preferred sets of system parameters selected according to at least one subjective expert opinion;

the image processor is configured to process the received signals into a number of images reflecting the subjective expert opinion;

generating, in a training data generator, sets of image variations for training based on different sets of system parameters; and, in a neural network:

processing data representing the images reflecting the subjective expert opinion and the image variations for training, for each set of image variations for training, auto-identifying image features that correlate to image features of the images reflecting the subjective expert opinion, and creating a trained network comprising the auto-identified image features, wherein the trained network is configured to use the auto-identified image features to provide corrections for system parameters, said corrections predicting how to modify system parameters to obtain system parameters reflecting desired subjective expert image preferences.

27. The method according to claim 26, further comprising using, an expert unit, the trained network to modify current system parameters of an imaging system based on the predicted corrections of the system parameters and to use the modified system parameters for creating new images.

28. The method according to claim 26, wherein the neural network is a convolutional neural network or recurrent neural network.

29. The method according to claim 27, further comprising generating, in the training data generator, the sets of system parameters according to a predetermined algorithm.

30. The method according to claim 27, further comprising, in the training data generator, using an algorithm that randomly samples system parameter values around the system parameters selected according to at least one subjective expert opinion to generate the sets of system parameters.

31. The method according to claim 27, wherein the data representing the images is one-dimensional, two-dimensional data, three-dimensional data, or four-dimensional data, wherein the data includes spatial and/or temporal data.

32. The method according to claim 27, wherein the imaging system comprises at least one of a Ultrasound system, an MRI (magnetic resonance imaging) system, a CT (computed tomography) system, an XR (X-ray radiation) system, a fluoroscopy imaging system, a PET (positron emission tomography) system, or a mammography imaging system.

\* \* \* \* \*